United States Patent [19]

Milgram et al.

[11] Patent Number: 5,387,615
[45] Date of Patent: Feb. 7, 1995

[54] L-DEPRENYL FOR TREATING IMMUNE SYSTEM DYSFUNCTION AND COMPOSITIONS FOR SAME

[75] Inventors: Norton W. Milgram, Scarborough, Canada; David R. Stevens, Leawood, Kans.; Gwendolyn O. Ivy, Scarborough, Canada

[73] Assignee: Deprenyl Animal Health, Inc., Overland Park, Kans.

[21] Appl. No.: 113,608

[22] Filed: Aug. 27, 1993

Related U.S. Application Data

[63] Continuation of Ser. No. 975,284, Nov. 12, 1992, Pat. No. 5,276,057, which is a continuation-in-part of Ser. No. 643,452, Jan. 18, 1991, abandoned, which is a continuation-in-part of Ser. No. 576,011, Aug. 31, 1990, Pat. No. 5,151,449.

[51] Int. Cl.$^6$ ............................................. A61K 31/135
[52] U.S. Cl. ......................................................... 514/654
[58] Field of Search ........................................... 514/654

[56] References Cited

U.S. PATENT DOCUMENTS

| | | | |
|---|---|---|---|
| 4,564,706 | 1/1986 | Ecsery et al. | 564/376 |
| 4,861,800 | 8/1989 | Buyske | 514/646 |
| 4,871,550 | 10/1989 | Millman | 424/601 |
| 4,880,883 | 11/1989 | Knoll et al. | 514/565 |
| 4,916,151 | 4/1990 | Berg et al. | 514/419 |
| 5,192,808 | 3/1993 | Ruehl et al. | 514/654 |
| 5,276,057 | 1/1994 | Milgram | 514/654 |

FOREIGN PATENT DOCUMENTS 871155  5/1971  Canada.
1215394 12/1986  Canada.

OTHER PUBLICATIONS

Milgram, et al., "Maintenance on L–Deprenyl Prolongs Life in Aged Male Rats", *Life Sciences*, vol. 47, 190, pp. 415–420 (1987).

Knoll, "Extension of Life Span of Rats by Long-Term (—) Deprenyl Treatment", *The Mount Sinai Journal of Medicine*, vol. 55, No. 1, Jan. 1988, pp. 67-74.

Knoll, "The Striatal Dopamine Dependency of Life Span in Male Rats, Longevity Study with (—) Deprenyl", *Mechanisms of Aging and Developments*, 46, (1988), 237-262.

Knoll, "The Pharmacology of Selective Mao Inhibitors", *Monoamine Oxidase Inhibitors—The State of the Art*, 1981, pp. 45-61.

Knoll, et al., "Long-Lasting, True Aphrodisiac Effect of (—)Deprenyl in Sexually Sluggish Old Male Rats", *Modl Probl. Pharmacopsychiat.*, vol. 19, pp. 135, 153 (1983).

*Primary Examiner*—Raymond Henley, III
*Assistant Examiner*—T. J. Criares
*Attorney, Agent, or Firm*—Zarley, McKee, Thomte, Voorhees & Sease

[57] ABSTRACT

Use of L-deprenyl for treatment of immune system dysfunction for mammals.

5 Claims, 1 Drawing Sheet

L-DEPRENYL FOR TREATING IMMUNE SYSTEM DYSFUNCTION AND COMPOSITIONS FOR SAME

CROSS REFERENCE TO RELATED APPLICATION

This is a continuation of application Ser. No. 07/975,284 filed on Nov. 12, 1992, now U.S. Pat. No. 5,276,057, which is a CIP of Ser. No. 07/643,452 filed on Jan. 18, 1991, now abandoned, which is a CIP of Ser. No. 07/576,011, filed on Aug. 31, 1990, now U.S. Pat. No. 5,151,449.

BACKGROUND THE INVENTION

L-deprenyl is a selective monoamine oxidase B (MAO-B) inhibitor, which is widely used as an adjunct in the treatment of Parkinson's disease. While its most common usage is for the treatment of Parkinson's disease, L-deprenyl was originally developed as an antidepressant agent. Recent testing has indicated that L-deprenyl may have some effect on increasing sexual response in aging animals, and also may have some effect, at least in rats in increasing life expectancy. However, to date L-deprenyl has only been medically approved by regulatory agencies for use as a treatment for Parkinson's disease in humans.

Parkinson's disease is a distinct disease associated with depletion of dopamine in the basal ganglia area of the brain, and the cardinal signs relate to motor dysfunction. Parkinson's disease is one of the most common causes of disability in older humans, with approximately 1% of persons being afflicted after age 60 (Jankovic, J. Parkinsonism. In: *Conn's Current Therapy* 1992; R. Rakel (ed.), W. B. Saunders Co., page 880, 1992). The cardinal signs involve various motor deficits, sometimes complicated by either neurobehavioral or other non-motor problems. Typical pathologic lesions of Parkinson's disease include neuronal "dropout" and the presence of Lewey bodies in the substantia nigra. The disease is considered progressive, despite advances in therapy. L-dopa replacement therapy is the primary medical treatment, although l-deprenyl and anticholinergics are also used in Parkinson's disease therapy.

Parkinson's disease is normally not thought of as a disease of immune system dysfunction although there are some literature reports discussing immune system abnormalities in Parkinson's disease. However, many Parkinson's Disease patients do show quite normal immune system function. Furthermore, there are no known reports of using l-deprenyl to treat immune system abnormalities. The limited reports of immune system dysfunction in Parkinsonians have been inconsistent, and tend to identify immune system problems in chronically PD-afflicted persons, the same persons who have received extended therapy with l-dopa. It is known that l-dopa may cause T-lymphocyte functional abnormalities in mice (Boukhris, W., Kouassi, E. et al. Impaired T-Dependent Immune Response in L-Dopa Treated BALB/C Mice. *J. Clin. Lab. Immunol.* 23(4). p. 185–189, 1987). Thus, the immune system abnormalities seen in some cases of PD may be caused by chronic l-dopa therapy. Since l-deprenyl is used to augment l-dopa therapy, it would be reasonable to conclude that ldeprenyl therapy would increase rather than decrease any immune system abnormalities in PD. To our knowledge, there are no published reports discussing l-deprenyl and its effect on the immune system function in either health or disease states, and there are no published reports describing the treatment of immune system dysfunction in any species with l-deprenyl.

Immune system dysfunction can and does occur at any stage of life due to a variety of causes, including aging (see p. 10–13). In many animals, i.e., man, dogs, monkeys, etc., immune system dysfunction, particularly as the animal ages, can substantially increase disease risk, which can threaten life itself. It is therefore important for over all well being to effectively treat any immune system dysfunction. Doing so will retard the risk of diseases known to affect animals with lowered immune response.

There is, therefore, a continuing and real need for the development of medications which treat immune system dysfunction.

In the grandparent application of co-inventor Milgram, now U.S. Pat. No. 5,151,449, there are disclosed certain uses of L-deprenyl for retardation of normal age dependent deterioration of renal function, retardation of normal degeneration of cognitive abilities, and for retardation of age dependent weight loss. In accordance with the improvement invention of parent application Ser. No. 07/643,452, it had been discovered that L-deprenyl will also assist in maintenance of thyroid function, adrenal function, immune system function and maintenance of body composition in aging mammals, providing that certain doses and levels of use were maintained. It may also be useful in treating Cushing's disease, (see Ruehl, Therapeutic Effect of L-Deprenyl In The Management of Pituitary-Dependant Hyperadrenocorticism (Cushing's Disease) filed Mar. 27, 1992).

While L-deprenyl is a known compound, it has never before been demonstrated effective and used at any level to treat immune system dysfunction.

Like most drugs, L-deprenyl can have diverse physiological effects which are completely dependent upon the dose administered. In accordance with the present invention, L-deprenyl can be used for successful methods of treatment for immune system dysfunction, providing that it is used at the dosage levels mentioned herein, and providing it is administered at the periodic intervals and for the length of time mentioned herein. Obviously, when different dosages and levels of treatment are used, the results expressed herein may not be achieved. In fact, at higher doses, adverse behavioral effects may be encountered.

Accordingly, a primary objective of the present invention is to develop a dosage regimen for use of L-deprenyl to treat immune system dysfunction in mammals.

The method and means of accomplishing this as well as other primary objectives of the present invention will be apparent from the detailed description which will follow hereinafter.

SUMMARY OF THE INVENTION

Figure 1:
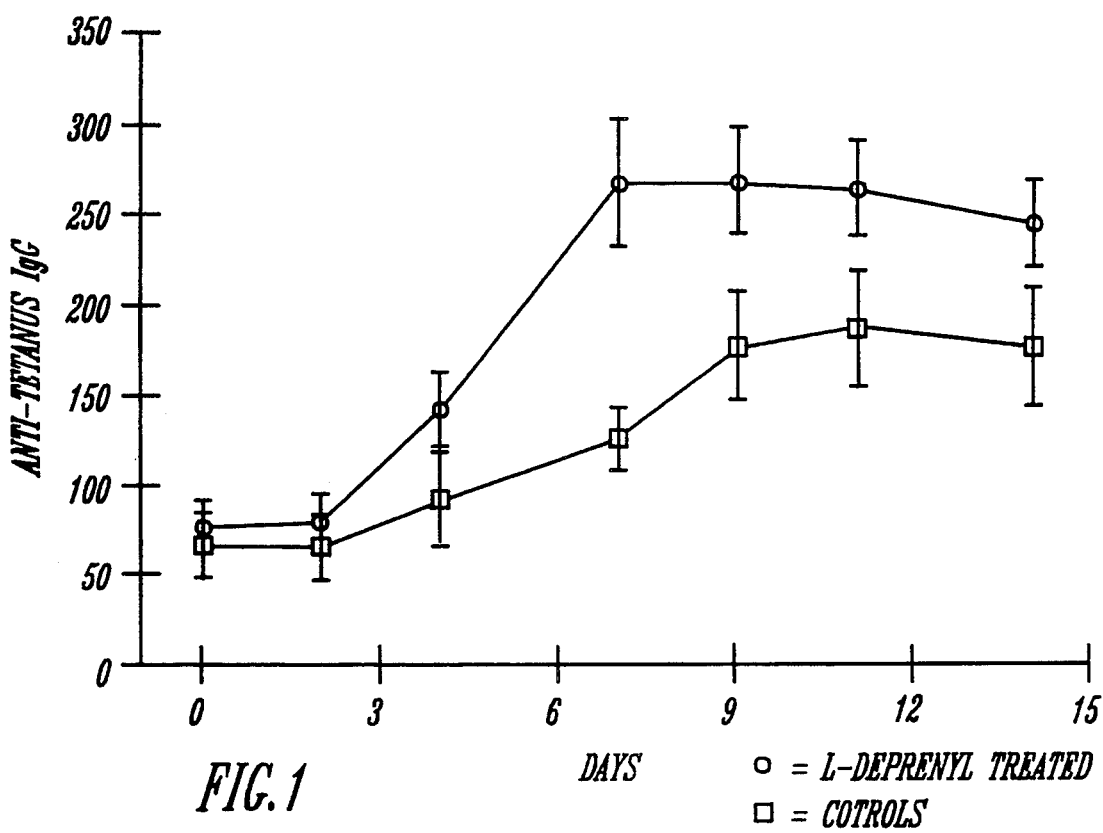
FIGS. 1 and 2 show the IgG and IgA levels after the treatment of Example 3.

The present invention relates to the process of using a known compound, L-deprenyl, for treating immune system dysfunction in mammals. In particular, at the dosage levels described herein, providing that the dosage is used for at least the periods of time expressed herein, there is an observed and measurable effect upon a dysfunctioning immune system. The treatment is shown to be useful for domesticated pets such as dogs, as they increase in age, but would be expected to have a like utility in any mammalian species, including humans.

DETAILED DESCRIPTION OF THE INVENTION

As earlier stated, the compound that is useful for the method or protocol of the present invention is a known compound, L-deprenyl. L-deprenyl has the formula (-)-N-a-dimethyl-N-2-propynylbenzene-ethanamine. It can be illustrated by the following graphic formula:

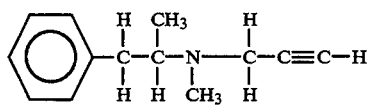

L-deprenyl also is at times referred to as (-)deprenyl to illustrate that it is a levorotary isomer. Typically, it is provided in a pharmaceutically acceptable salt form thereof such as the hydrochloride salt.

As used here, pharmaceutically acceptable salt form thereof, means the following. Acceptable for use in the pharmaceutical or veterinary art, being nontoxic or otherwise not pharmaceutically or veterinary unacceptable. "Acceptable salt form thereof" means salts formed with inorganic acids such as hydrochloric acid, hydrobromic acid, sulfuric acid, nitric acid, phosphoric acid, and the like, and as well organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, etc.

Administration of the therapeutically active compound l-deprenyl to achieve physiological results of the present invention can be via any of the accepted modes of administration for systemically active substances. These methods include oral, parenteral, and otherwise systemic, aerosol, and topical forms, as well as sustained release systems, etc.

The compositions of the present invention may be any of those known in the pharmaceutical and veterinary arts which are suitable for the method of administration and dosage required in any particular circumstance. In the case of both pharmaceutical and veterinary applications, such compositions may include tablets, pills, capsules, powders, aerosols, suppositories, skin patches, parenterals, and oral liquids including oil aqueous suspensions, solutions and emulsions. It may include long acting injectables and sustained release devices.

When the dosage is in solid form, solid pharmaceutical carriers such as starch, sugar, talc, mannitol, povidone, magnesium stearate, and the like may be used to form powders. Lactose and mannose are the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of l-deprenyl, advisably as a nontoxic acid addition salt, and may be administered one or more at a time at regular intervals as later described. Such unit dosage forms, however, should with a broad range guideline contain a concentration of 0.1 mg/kg to 5.0 mg/kg of the active l-deprenyl.

A typical tablet for the specified uses mentioned herein in a 25 kg dog may have the composition:

|   | Mg. |
| --- | --- |
| 1. L-deprenyl | 25 |
| 2. Mannitol | 100 |
| 3. Stearic acid | 3 |

A granulation is made from the mannitol. The other ingredients are added to the dry granulation and then the tablets are punched.

Another tablet may have the composition:

|   | Mg. |
| --- | --- |
| 1. L-deprenyl | 25 |
| 2. Starch U.S.P. | 57 |
| 3. Lactose U.S.P. | 73 |
| 4. Talc U.S.P. | 9 |
| 5. Stearic acid | 6 |

Powders 1,2 and 3 are slugged, then granulated, mixed with 4 and 5, and tableted.

Capsules may be prepared by filling No. 3 hard gelatin capsules with the following ingredients, thoroughly mixed:

|   | Mg. |
| --- | --- |
| 1. L-deprenyl | 25 |
| 2. Lactose U.S.P. | 200 |
| 3. Starch U.S.P. | 16 |
| 4. Talc U.S.P. | 8 |

As earlier expressed, physiological functions affected by the treatment herein with L-deprenyl are necessarily dosage dependent. Put another way, like most drugs, l-deprenyl has diverse physiological effects depending upon the dose administered. Unless the dose administered is within the levels set forth herein, the desired effects on immune function, without adverse effects, are not achieved.

Immune reactions involve the coordinated efforts of several types of cells, such as T and B lymphocytes and macrophages. Substantial evidence exists in several species that immune dysfunction occurs with increasing age and that impaired T-cell function may be one of the mechanisms for the decline. While some changes in B lymphocyte function have been reported, it is difficult to dissociate these effects from concomitant changes in T-Cells. Also, little or no evidence supports changes in antigen presenting cells (macrophages) with increasing age. On the other hand, a number of investigators have shown a substantial decline in most measures of T-cell function with age.

The most studied of the immune parameters is lymphocyte proliferation. The proliferative capacity of both T- and B-cells has been found to decline substantially with increasing age (Morgan et al., "The immune response in aged C57BL/6 mice. I. Assessment of lesions in the B-cell and T-cell compartments of aged mice utilizing the Fc fragment-mediated polyclonal antibody response", *Cellular Immunology* 63, 16–27, 1981; Abraham et al., "Reduced in vitro response to concanavalin A and lipopolysaccharide in senescent mice: A function of reduced number of responding cells", *European Journal of immunology*, 7, 301–304, 1977; Hefton et al., "Immunologic studies of aging. V. Impaired proliferation of PHA responsive human lymphocytes in culture", *Journal of Immunology* 125, 1007–1010, 1980). These studies utilize splenocytes which are mitogenically challenged with phytohemaglutin (PHA) or concanavalin-A in vitro in the presence of 3H-thymidine or bromodeoxyuridine (BrdU). Thymidine or BrdU uptake by the cells is then measured and reflects the number of cells entering mitosis. Also, upon activation by mitogens or antigens, T-cells secrete a number of antigen-non-specific growth and maturation factors, collectively termed lymphokines. One of these, Interleukin-2 (IL-2), seems to be required for T-cell division and plays a role in B-cell growth as well. T-cells from old mice and humans have been found to secrete diminished amounts of IL-2 when triggered by mitogens, alloantigens or foreign antigens (Gillis et al., "Immunological studies of aging. Decreased production of and response to T cell growth factor by lymphocytes from aged humans", *Journal of Clinical Investigation* 67, 937–942, 1981; Miller and Stutman, "Decline, in aging mice, of the anti-TNP cytotoxic T cell response attributable to loss of Lyt-2, IL-2 producing helper cell function", *European Journal of Immunology* 11, 751–756, 1981; Nagel et al., "Decreased proliferation, interleukin 2 synthesis, and interleukin 2 receptor expression are accompanied by decreased mRNA expression in phytohemagglutinin-stimulated cells from elderly donors", *Journal of Clinical Investigation* 81, 1096–1102, 1988; Thomas and Weigle, "Partial restoration of Con A-induced proliferation, IL-2 receptor expression, and IL-2 synthesis in aged murine lymphocytes by phorbol myristate acetate and ionomycin", *Cellular Immunology* 114, 1–11, 1988). Further, several studies have shown that aging leads not only to poor production of IL-2, but also to diminished responsiveness to this growth factor. Thus, addition of exogenous IL-2 leads to only a partial restoration of function in immune cells from old animals (Gillis et al., "Immunological studies of aging. Decreased production of and response to T cell growth factor by lymphocytes from aged humans", *Journal of Clinical Investigation* 67, 937–942, 1981; Gilman et al., "T lymphocytes of young and aged rats. II. Functional defects and the role of interleukin-2", *Journal of Immunology* 128, 644–650, 1982; Gottosman et al., "Proliferative and cytotoxic immune functions in aging mice. III. Exogenous interleukin-2 rich supernatant only partially restores alloreactivity in vitro", *Mechanisms of Ageing and Development* 31, 103–113, 1985). Also, the number of T-cells able to express IL-2 receptors upon stimulation by a mitogenic agent declines with age in both humans and mice (Negoro et al., "Mechanisms of age-related decline in antigen specific T cell proliferative response: IL-2 receptor expression and recombinant IL-2 induced proliferative response of purified TAC-positive T cells", *Mechanisms of Ageing and Development* 36, 223–241, 1986; Vie and Miller, "Decline, with age, in the proportion of mouse T cells that express IL-2 receptors after mitogen stimulation", *Mechanisms of Ageing and Development* 33, 313–322, 1986). Aging, therefore, leads to a decline in both production of and response to IL-2.

It has also been reported that older dogs produce less antibody to an exogenous T-lymphocyte dependent antigen, sheep red blood cells, than younger dogs (Bice, D. and Muggenburg, B. "Effect of Age on Antibody Responses after Lung Immunization", *American Revue of Respiratory Disease.* 132:661–665, 1985). This was indicative of the normal age-related decline in immune system function, or age-related immune system dysfunction, that is documented in various species, including dogs, rodents, non-human primates and humans.

The term "mammal" as used herein includes without limitation humans and domesticated animals such as cattle, horses, swine, sheep, dogs, cats, goats and the like. The tests hereinafter shown in the examples are particularly illustrative for dogs, but indicate usage for humans as well as for domesticated animals including cats and other mammals. The treatment may even work for birds or fish.

Needless to say, the natural enjoyment of pets would be significantly increased in their older age if their general well being and and health is maintained. This requires a healthy, functioning immune system.

In accordance with the present invention, it is illustrated that immune system response can be improved if the animal is treated periodically with small but therapeutically effective doses of l-deprenyl.

As hereinafter explained, the dosage regimen to achieve these desirable results differs considerably from the dosage regimen used in treating Parkinson's disease and may differ in quantity and frequency from the dose levels in the parent application, Milgram, Ser. No. 07/576,011 filed Aug. 31, 1990. At the preferred dose recommended for uses disclosed herein, the levels are up to 25X the amount used for treating Parkinson's disease. In particular, the dosage regimen of the present invention shows usage at levels from about 0.1 mg/kg of body weight up to about 5.0 mg/kg of body weight from 1 to 7 times weekly, preferably daily. Most preferably the dosage level is 0.5–2.0 mg/kg of body weight given once daily. Of course it would be known to those in the art that sustained release systems can be used to provide less frequent administration to achieve the required dosage level.

It is not known precisely why the use of l-deprenyl at the dosage levels and periodicity expressed herein achieves these results. As explained in the examples below, analysis of blood specimens suggests that the l-deprenyl treatment may have a direct effect on the immune system specifically. It is important that the dosage be at levels expressed herein rather than at Parkinson's disease levels, otherwise no beneficial effects may be achieved.

EXAMPLES

The following examples provide illustrative evidence of the results for treating mammals with l-deprenyl for immune system dysfunction.

EXAMPLE 1

Example of Maintaining Peripheral Blood White Cell and Lymphocyte Counts in Aging Fischer Rats Sixty two male Fischer 344 rats were obtained at 21–23 months of age. The animals were allowed free access to food and water. L-deprenyl was injected subcutaneously every other day at a dose of 0.25 mg/kg body weight, starting at 24–25 months of age. Thirty one rats were given the l-deprenyl, and thirty one rats served as sham-injected controls (given saline).

Blood samples were collected on all rats at the beginning of the experiment and again from surviving rats after three months of l-deprenyl therapy. The blood samples were sent to a local commercial clinical pathology laboratory for routine hematological testing. A double blind procedure was followed in the collection and analysis of the blood samples.

As these F344 rats become older, there is a trend for abnormal increases in peripheral blood lymphocytes, which may be associated with and indicative of immune system dysfunction. In the rats receiving l-deprenyl, there was a distinct inhibition in the proliferation of peripheral blood lymphocytes, which might be expected with age-related immune system dysfunction. The data is presented in Table 1. These results indicate that chronic l-deprenyl therapy may be beneficial in age-related immune system dysfunction in rats.

TABLE 1

|  | Baseline (24–25 months) | | 27–29 Months | |
| --- | --- | --- | --- | --- |
|  | Control | l-Deprenyl | Control | L-Deprenyl |
| WBC count* | 5.32 ± .94 | 5.20 ± .43 | 15.89 ± 5.03 | 8.45 ± 1.6 |
| Lymphocyte count* | 2.16 ± .31 | 2.15 ± .29 | 10.64 ± 4.47 | 4.12 ± 1.27 |

*numbers are × 10 to the 6th per ml. of blood

EXAMPLE 2

Example of Treating Age-Related Immune System Dysfunction

Old (12 to 16 years) laboratory beagles of either sex were divided into twelve animals per group. Similar laboratory beagles have been shown to have age-related immune system dysfunction, as manifested by significantly lower antibody responses to the exogenous antigen, sheep red blood cells (Bice, D. and Muggenburg, B. "Effect of Age on Antibody Responses after Lung Immunization", Am. Rev. Resp. Dis. 132: 661–665, 1985). The experimental group received 1 mg/kg of l-deprenyl every day via oral tablets for approximately six months.

Lymphocyte subset data was developed to determine whether the age-related immune system dysfunction characterized by a decrease in the helper/suppressor lymphocyte ratio might be treated by l-deprenyl administration. This data was developed using monoclonal antibodies to specific lymphocyte cell surface antigens using standard cell sorting (flow cytometry) techniques (Moore, P. F. et al. Monoclonal Antibodies Specific for Canine CD4 and CD8 define functional T lymphocyte subsets and high-density expression of CD4 by canine neutrophils, Tissue Antigens 40: 75–85, 1992.)

The below set forth data Table 2 provides the results. Note particularly the CD4/CD8 ratio of 2.5 in young dogs; 1.37 in old untreated dogs; and 1.89 in old l-deprenyl treated dogs. This example demonstrates that the peripheral blood lymphocyte "helper cell" to "suppressor cell" ratio, which often decreases with increasing age (and which may help explain age-related immune system dysfunction), is amenable to chronic l-deprenyl therapy. Treating the age-related decrease in the helper/suppressor cell ratio with l-deprenyl therapy may partially explain why older dogs with immune system dysfunction are able to mount a statistically increased humoral antibody response to an T-lymphocyte dependent antigen such as tetanus toxoid (see. Example 3, below).

TABLE 2

Effect of L-Deprenyl on T-Lymphocyte Subsets in Aging Dogs

| Group | T-Lymphocyte Subsets | | |
| --- | --- | --- | --- |
|  | CD4 | CD8 | CD4/CD8 Ratio |
| 1. Young Control Dogs | 53.6 ± 6.6 | 21.8 ± 4.3 | 2.56 ± 0.64 |
| 2. Old Control Dogs | 31.8 ± 6.8 | 26.3 ± 9.2 | 1.37 ± 0.56 |
| 3. L-Deprenyl Treated Old Dogs | 39.4 ± 11.3 | 23.7 ± 9.1 | 1.89 ± 0.86 |

EXAMPLE 3

Example of Humoral Antibody Response to Tetanus Toxoid

Old (12 to 16 years) laboratory beagles of either sex were divided into twelve animals per group. Similar laboratory beagles have been shown to have age-related immune system dysfunction, as manifested by significantly lower antibody responses to the exogenous antigen, sheep red blood cells (Bice, D. and Muggenburg, B. "Effect of Age on Antibody Responses after Lung Immunization", Am. Rev. Resp. Dis. 132: 661–665, 1985). The experimental group received 1 mg/kg of l-deprenyl every day via oral tablets for approximately six months.

The immune system of each animal was challenged with 0.5 ml of commercially available tetanus toxoid by subcutaneous inoculation on day 0 and day 21. The inoculations were given on Jul. 27th and Aug. 17th, 1992.

The immune response was evaluated using an enzyme-linked immunosorbent assay ("Elisa") using standard methods known in the art (Brice, D. and Muggenburg, B. "Effect of Age on Antibody Responses after Lung Immunization", Am. Rev. Resp. Dis. 132: 661–665, 1985).

The immune response evaluation schedule occurred on days 3,5,7,9,11 and 14 after the first inoculation and days 2,4,7,9,11 and 14 after the second inoculation.

The T-lymphocyte dependent antigen tetanus toxoid was used in these tests to determine whether or not l-deprenyl administration bolster-ed the systemic immune response in aged dogs. The serum antibody levels (IgA and IgG) were measured. The synthesis and the secretion of these antibodies in the blood is indicative of the integrity of the immune response and provides a quantitative assessment of the magnitude of the response, with higher levels of antibodies representing a more robust systemic immune system and response and lower antibody levels representing a relative dysfunction of the immune system.

The data was statistically analyzed using ANOVA (analysis of variance) comparison on individual days and repeated measures ANOVA over the entire time course.

Figure 2:
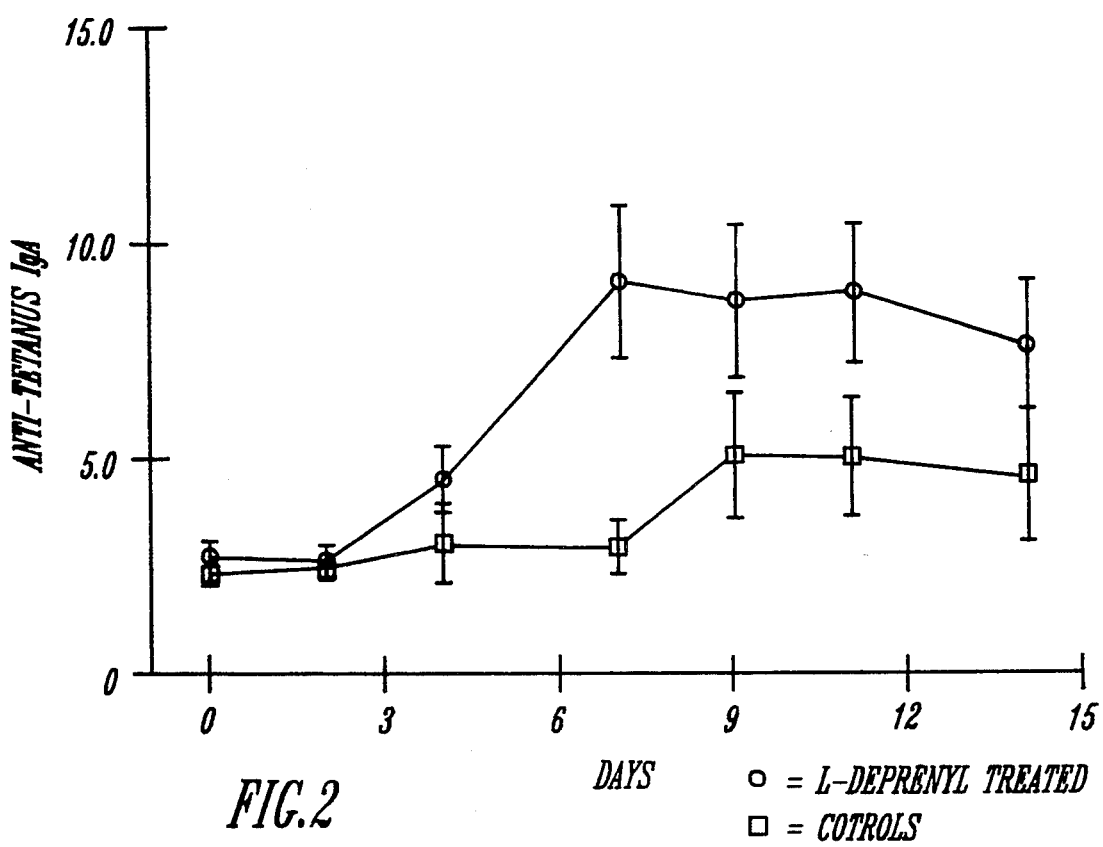

There was no statistically significant difference between the experimental and the control groups at time zero. After the first inoculation the l-depreynl treated group exhibited a trend toward greater levels of specific serum IgG and IgA, although statistical significance was not achieved. However, the experimental dogs that had been given l-deprenyl for six months had statistically significant increases in specific anti-tetanus serum IgA and serum IgG after the second (booster) inoculation as shown in FIGS. 1 and 2.

These results indicate that old dogs that have been given 1 mg/kg of body weight of l-deprenyl for approximately six months, have a statistically significant increase in humoral systemic immune response (IgA and IgG) to tetanus toxoid after the booster dose, as compared to control dogs. The administration of l-deprenyl at 1 mg/kg to aged dogs improved the systemic response to a test foreign antigen, tetanus toxoid. There is therefore a statistically significant, effective treatment of immune system dysfunction in these older animals if they are provided with l-deprenyl at the dose levels of the present invention for significant periods of time.

What is claimed is:

1. A method of treating immune system dysfunction of humans by stimulating a secretion selected from the group consisting of Tumor Necrosis Factor alpha, Interleukin-6 and Granulocyte-Macrophage Colony Stimulating Factor, said method comprising:

administering to the human a dose level greater than level used to treat Parkinson's disease and an immune response dysfunction treating effective amount of the compound L-deprenyl, or a pharmaceutically acceptable form thereof, at a frequency level of from about one to about seven times weekly until a desired effect upon deterioration of immune system response function is achieved.

2. The method of claim 1 wherein the L-deprenyl is the hydrochloride addition salt form thereof.

3. The method of claim 1 wherein the addition level is at a level of from 0.1 mg/kg of body weight to 5.0 mg/kg of body weight.

4. The method of claim 3 wherein the addition level is from about 0.1 mg/kg of body weight to about 5.0 mg/kg of body weight, dosed from one to seven times weekly.

5. A method of treating immune system dysfunction of hormoral antibody response and T lymphocyte function of mammals, said method comprising:

administering to the mammal a small but humoral antibody response and T lymphocyte dysfunction treating effective amount of the compound L-deprenyl, or a pharmaceuticall acceptable form thereof, at a frequency level of from about one to about seven times weekly until a desired effect upon deterioration of immune system response function is achieved.

* * * * *